(12) United States Patent
Morris et al.

(10) Patent No.: US 7,232,218 B2
(45) Date of Patent: Jun. 19, 2007

(54) BIFOCAL MULTIORDER DIFFRACTIVE LENSES FOR VISION CORRECTION

(75) Inventors: G. Michael Morris, Victor, NY (US); Dale A. Buralli, Rochester, NY (US); Richard J. Federico, Churchville, NY (US)

(73) Assignee: Apollo Optical Systems, Inc., Rochester, NY (US)

( * ) Notice: Subject to any disclaimer, the term of this patent is extended or adjusted under 35 U.S.C. 154(b) by 249 days.

(21) Appl. No.: 10/973,041

(22) Filed: Oct. 25, 2004

(65) Prior Publication Data

US 2005/0057720 A1   Mar. 17, 2005

Related U.S. Application Data

(62) Division of application No. 10/462,294, filed on Jun. 16, 2003, now Pat. No. 6,951,391.

(51) Int. Cl.
*G02C 7/06* (2006.01)

(52) U.S. Cl. ............... 351/168; 351/161; 623/6.3; 359/558

(58) Field of Classification Search ......... 351/159, 351/160 R; 623/6.3, 6.31; 359/558
See application file for complete search history.

(56) References Cited

U.S. PATENT DOCUMENTS

| | | |
|---|---|---|
| 3,004,470 A | 10/1961 | Ruhle |
| 4,162,122 A | 7/1979 | Cohen |
| 4,210,391 A | 7/1980 | Cohen |
| 4,338,005 A | 7/1982 | Cohen |
| 4,340,283 A | 7/1982 | Cohen |
| 4,541,697 A | 9/1985 | Remijan |
| 4,637,697 A | 1/1987 | Freeman |
| 4,641,934 A | 2/1987 | Freeman |
| 4,642,112 A | 2/1987 | Freeman |
| 4,655,565 A | 4/1987 | Freeman |
| 4,769,033 A | 9/1988 | Nordan |
| 4,830,481 A | 5/1989 | Futhey et al. |
| 4,881,804 A | 11/1989 | Cohen |
| 4,881,805 A | 11/1989 | Cohen |
| 4,936,665 A | 6/1990 | Whitney |

(Continued)

OTHER PUBLICATIONS

Nordan, L., The Vision Membrane, Cataract & Refractive Surgery Today (2003).

(Continued)

*Primary Examiner*—Jordan M. Schwartz
(74) *Attorney, Agent, or Firm*—Kenneth J. Lukacher (57) ABSTRACT

A bifocal multiorder diffractive lens having a lens body with one or more first regions having a first multiorder diffractive structure providing near vision correction, and one or more second regions having a second multiorder diffractive structure providing distance vision correction, in which the lens defines an aperture divided between the first and second regions. The lens body may be provided by a single optical element or multiple optical elements. In other embodiments, a bifocal multiorder diffractive lens is provided by a single or multiple element lens body having a multiorder diffractive structure for distance vision correction and one or more refractive regions to add power for near vision correction, or a single or multiple element lens body shaped for refractive power for distance vision correction and a multiorder diffractive structure for add power for near vision correction. Multiorder diffractive structures may be optimized for photopic and scotopic vision.

30 Claims, 6 Drawing Sheets

U.S. PATENT DOCUMENTS

| | | |
|---|---|---|
| 4,936,666 A | 6/1990 | Futhey |
| 4,995,714 A | 2/1991 | Cohen |
| 4,995,715 A | 2/1991 | Cohen |
| 5,013,133 A | 5/1991 | Buralli et al. |
| 5,016,977 A | 5/1991 | Baude et al. |
| 5,017,000 A | 5/1991 | Cohen |
| 5,054,905 A | 10/1991 | Cohen |
| 5,056,908 A | 10/1991 | Cohen |
| 5,071,207 A | 12/1991 | Ceglio et al. |
| 5,076,684 A | 12/1991 | Simpson et al. |
| 5,096,285 A | 3/1992 | Silberman |
| 5,100,226 A | 3/1992 | Freeman |
| 5,104,212 A | 4/1992 | Taboury et al. |
| 5,114,220 A | 5/1992 | Baude et al. |
| 5,116,111 A | 5/1992 | Simpson et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,129,718 A | 7/1992 | Futhey et al. |
| 5,144,483 A | 9/1992 | Cohen |
| 5,152,788 A | 10/1992 | Isaacson et al. |
| 5,153,778 A | 10/1992 | Sasian-Alvarado |
| 5,178,636 A | 1/1993 | Silberman |
| 5,198,844 A | 3/1993 | Roffman et al. |
| 5,229,797 A | 7/1993 | Futhey et al. |
| 5,237,451 A | 8/1993 | Saxe |
| 5,257,132 A | 10/1993 | Ceglio et al. |
| 5,281,294 A | 1/1994 | Freeman et al. |
| 5,285,314 A | 2/1994 | Futhey |
| 5,296,881 A | 3/1994 | Freeman |
| 5,344,447 A | 9/1994 | Swanson |
| 5,349,396 A | 9/1994 | Roffman et al. |
| 5,384,606 A | 1/1995 | Koch et al. |
| 5,408,281 A | 4/1995 | Zhang |
| 5,442,480 A | 8/1995 | Swanson et al. |
| 5,448,312 A | 9/1995 | Roffman et al. |
| 5,485,228 A | 1/1996 | Roffman et al. |
| 5,507,806 A | 4/1996 | Blake |
| 5,507,979 A | 4/1996 | Roffman et al. |
| 5,512,220 A | 4/1996 | Roffman et al. |
| 5,517,260 A | 5/1996 | Glady et al. |
| 5,574,518 A | 11/1996 | Mercure |
| 5,589,982 A | 12/1996 | Faklis et al. |
| 5,682,223 A | 10/1997 | Menezes et al. |
| 5,684,560 A | 11/1997 | Roffman et al. |
| 5,699,142 A | 12/1997 | Lee et al. |
| 5,715,031 A | 2/1998 | Roffman et al. |
| 5,724,120 A | 3/1998 | Svochak et al. |
| 5,724,258 A | 3/1998 | Roffman |
| 5,748,282 A | 5/1998 | Freeman |
| 5,760,871 A | 6/1998 | Kosoburd et al. |
| 5,798,817 A | 8/1998 | de Carle |
| 5,800,532 A | 9/1998 | Lieberman |
| 5,805,260 A | 9/1998 | Roffman et al. |
| 5,847,802 A | 12/1998 | Menezes et al. |
| 5,895,422 A | 4/1999 | Hauber |
| 5,929,969 A | 7/1999 | Roffman |
| 6,120,148 A | 9/2000 | Fiala et al. |
| 6,139,147 A | 10/2000 | Zhang |
| 6,176,878 B1 | 1/2001 | Gwon et al. |
| 6,179,420 B1 | 1/2001 | Roffman et al. |
| 6,231,603 B1 | 5/2001 | Lang et al. |
| 6,250,757 B1 | 6/2001 | Roffman et al. |
| 6,270,220 B1 | 8/2001 | Keren |
| 6,325,510 B1 | 12/2001 | Golub et al. |
| 6,330,110 B2 | 12/2001 | Nakai |
| 6,364,483 B1 | 4/2002 | Grossinger et al. |
| 6,406,494 B1 | 6/2002 | Laguette et al. |
| 6,457,826 B1 | 10/2002 | Lett |
| 6,474,814 B1 | 11/2002 | Griffin |
| 6,511,178 B1 | 1/2003 | Roffman et al. |
| 6,560,019 B2 * | 5/2003 | Nakai .......................... 359/569 |
| 6,760,159 B2 * | 7/2004 | Nakai .......................... 359/576 |
| 6,831,783 B2 * | 12/2004 | Hoshi .......................... 359/569 |
| 6,937,397 B2 * | 8/2005 | Okuno et al. ................ 359/575 |
| 2001/0018612 A1 | 8/2001 | Carson et al. |
| 2002/0016630 A1 | 2/2002 | Lang |
| 2002/0120329 A1 | 8/2002 | Lang et al. |
| 2002/0143394 A1 | 10/2002 | Lang |
| 2002/0161435 A1 | 10/2002 | Portney |
| 2002/0193876 A1 | 12/2002 | Lang et al. |
| 2003/0014107 A1 | 1/2003 | Reynard |
| 2003/0018385 A1 | 1/2003 | Tran et al. |
| 2003/0035214 A1 | 2/2003 | Pandya |
| 2003/0045931 A1 | 3/2003 | Lang |
| 2003/0097176 A1 | 5/2003 | Nordan et al. |

OTHER PUBLICATIONS

Lipner, M., The near view on a new multifocal IOL, EyeWorld, p. 69 (2003).
CIBA Vision, Surgical Solutions, Vivarte PRESBYOPIC—Anterior Chamber Phakic Refractive Lens, http://www.cibavision.com/products/surgical_solutions/vivarte_presbyopic.shtml (2003).
Advanced Medical Optics, Inc. (AMO), Array, Silicone Multifocal Intraocular Lens, http://www.amo-inc.com/site/products/consumers/home.asp?id=array&largeText=(2003).
Iolteck, Le Multifocal, MF4 Implant Multifocal, http://www.ioltech.com/beta/fr/zoom/zmult.html (2003).
Iolteck, Newlife Multifocal Implant, http://www.ioltech.com/beta/fr/zoom/newlife.html (2003).
Golub, M., et al., Diffractive Optical Elements for Biomedical Applications, SPIE, vol. 3199, pp. 220-231 (1997).
Diffractive Focuser Into Focal Line Contour, http://www.holoor.co.il/data/ready2/products/mfr-multifocal/multil.htm (2004).
Beam Multiplication, RGP Multifocal Contact Lenses, http://www.holoor.co.il/data/ready2/products/rgb_bi_focal/rgb_multi_focal.htm (2004).
Beam Multiplication, Soft Multifocal Contact Lenses, http://www.holoor.co.il/data/ready2/products/rgb_bi_focal/rgb_softmulti_focal.htm (2004).
Golub, M. et al., Multifocal Contact and Intraocular Lenses with Diffractive Microrelief, The 10th Meeting on Optical Engineering in Israel, Nov. 1996.
Faklis, D. et al., Spectral properties of multiorder diffractive lenses, Applied Optics, vol. 34, No. 14, May 1995.

* cited by examiner

BIFOCAL MULTIORDER DIFFRACTIVE LENSES FOR VISION CORRECTION

This application is a divisional of U.S. patent application Ser. No. 10/462,294, filed Jun. 16, 2003, now U.S. Pat. No. 6,951,391.

FIELD OF THE INVENTION

The present invention related to multiorder diffractive lenses for vision correction, and particularly to bifocal multiorder diffractive lenses for therapeutic vision correction at distance and near vision correction suitable for use with a variety of vision correction applications, such as intraocular implants (IOLs), contact lenses, or spectacle (eyeglass) lenses.

BACKGROUND OF THE INVENTION

Multiorder diffractive (MOD) lenses are useful for bringing a plurality of spectral components of different wavelengths to a common focus, and are described in U.S. Pat. No. 5,589,982, which is herein incorporated by reference. The MOD lens has a structure of multiple annular zones having step heights defining zone boundaries, which diffract light of each of the wavelengths in a different diffractive order to a common focus. Such a MOD lens has not been applied to bifocal optics for vision correction.

Conventional bifocal optics for spectacles are provided by lenses having lower and upper regions of different refractive power for near and distance (far) vision correction. For contact lenses and IOLs, multifocal refractive optics have been proposed with the anterior and/or posterior surfaces of a lens (or IOL optic) shaped to provide a central zone, annular near zones, and annular distance zones of different refractive powers. Such bifocal refractive lenses do not utilize diffractive structures for near or distance vision correction. Examples of multifocal refractive lenses for contacts and IOLs are shown in U.S. Pat. Nos. 6,231,603, 5,805,260, 5,798,817, 5,715,031, 5,682,223, and U.S. Publication No. US2003/0014107 A1. Other multifocal refractive lenses have other zones, such as pie, hyperbolic, or pin-wheel shaped near and distance zones, as shown in U.S. Pat. Nos. 5,512,220 and 5,507,979, or spiral shaped zones, as shown in U.S. Pat. Nos. 5,517,260 and 5,408,281. Moreover, refractive lenses are generally thicker than diffractive lens for equivalent optical power, and thickness reduction is often desirable in ophthalmic applications, such as contact lenses and IOLs.

Non-MOD diffractive optics for multifocal ophthalmic applications exist having a lens with a surface providing a diffractive structure of concentric zones of different step heights for near and far vision correction, such as described, for example, in U.S. Pat. No. 5,699,142. Another multifocal diffractive lens, described in U.S. Pat. No. 5,748,282, has a similar diffractive structure with a region having a reduced step height to reduce intensity of light from such region. A further multifocal diffractive lens is described in U.S. Pat. No. 5,116,111 also has a similar non-MOD diffractive structure in which the base power of lens may be provided by refraction of the lens. The diffractive lenses of U.S. Pat. Nos. 5,699,142, 5,748,282, and 5,116,111 lack the ability of the MOD lens to focus light of different wavelengths to a common focus for either near or far vision correction by their reliance on non-MOD structures. Other non-MOD optics may be segmented to provide multiple regions, but are not multifocal. For example, U.S. Pat. No. 5,071,207 describes a non-MOD diffractive lens having pie-shaped segments in which all the segments of the lens are limited to focusing light to a common focus. Thus, prior approaches to multifocal or bifocal optics have utilized refractive surfaces or non-MOD structures.

SUMMARY OF THE INVENTION

Accordingly, it is the principal object of the present invention to provide bifocal diffractive lenses utilizing multiorder diffractive (MOD) structures to provide vision correction at near and far distances.

Another object of the present invention is to provide bifocal multiorder diffractive lenses which may be adapted for use in a variety of vision correction applications, including contact lenses, intraocular implants (IOL), and spectacle lenses.

Still another object of the present invention is to provide bifocal multiorder diffractive lenses using MOD structures which may have refractive surfaces for additional power correction.

A further object of the present invention is to provide a bifocal multiorder diffractive lens for correction of vision in which the performance of the lens is tailored to the human perception of light under high (photopic) and low (scotopic) illumination.

Briefly described, the present invention embodies a lens body having one or more first regions having a first multiorder diffractive structure providing near vision correction, and one or more second regions having a second multiorder diffractive structure providing distance vision correction, in which the lens defines an aperture divided between the first and second regions. Such one or more first regions may represent one or more annular rings, or other portion of the lens, and the second region may occupy the portion of the lens aperture outside the first region, such as central region and one or more annular rings alternating with first region annular ring(s). The lens may be a single optical element having the first and second regions both located upon the same front or back surface of the lens, or the first region located upon one of the front or back surface and the second regions on the other surface. The lens may also be provided by multiple optical elements integrated into the lens body having front and back surfaces and one or more intermediate surfaces depending on the number of optical elements. The first and second regions are provided along the same or different intermediate surfaces of the lens to divide the lens aperture. One or both of the first and second multiorder diffractive structures may be optionally optimized for performance for photopic and scotopic vision.

In other embodiments, a bifocal multiorder diffractive lens is provided by a single or multiple element lens body having a multiorder diffractive structure for distance vision correction and one or more refractive regions to add power for near vision correction, or a single or multiple element lens body shaped for refractive power for distance vision correction and a multiorder diffractive structure to add power for near vision correction.

Each of the MOD structures of the lenses of the present invention directs different wavelengths of light to a single focus of an optical power for the desired vision correction. This MOD structure is characterized by multiple zones which define zone boundaries at which light incident on the diffractive structure experiences an optical phase shift, and diffracts light of each of the wavelengths in a different diffractive order, m, such that m is greater than or equal to 1, to the same focus. The zones may be radially spaced at $r_j$ and said radii are obtained by solving the equation $\phi(r_j) = 2\pi pj$ where $\phi(r_j)$ represents the phase function for the wavefront emerging from the diffractive lens, and p represents the number of $2\pi$ phase jumps at the zone boundaries for one of the plurality of wavelengths where p is an integer greater than 1. The MOD structure is described in more detail in the above-incorporated U.S. Pat. No. 5,589,982.

The lenses of the present invention may be used in a variety of ophthalmic applications, such as a contact lens, a spectacle lens, or the lens of an intraocular implant (IOL), or other optics useful for vision correction of the eye.

DETAILED DESCRIPTION OF THE DRAWINGS

The foregoing objects, features and advantages of the invention will become more apparent from a reading of the following description in connection with the accompanying drawings, in which.

DETAILED DESCRIPTION OF THE INVENTION

Figure 1A:
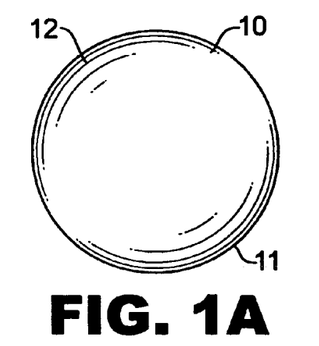
FIGS. 1A and 1B are plan diagrams of the two surfaces of a first embodiment bifocal multiorder diffractive lens of the present invention in which two different multiorder diffractive structures are provided on the surface of FIG. 1B for near and distance vision correction, and no diffractive structures are provide on the surface of FIG. 1A.
Figure 1B:
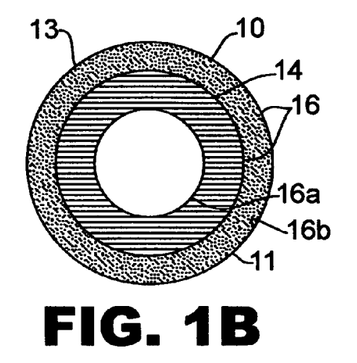
Figure 1C:
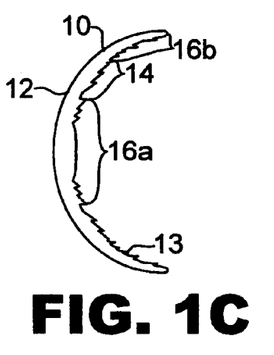
FIG. 1C is a sectional view of the lens of FIGS. 1A and 1B.
Figure 2A:
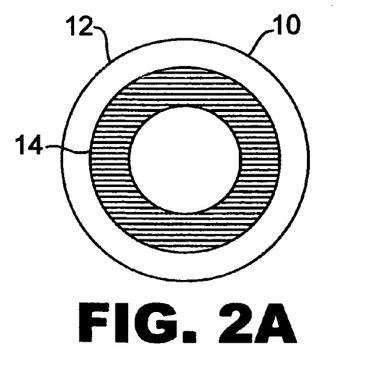
FIGS. 2A and 2B are plan diagrams of the two surfaces of a second embodiment bifocal multiorder diffractive lens of the present invention in which one multiorder diffractive structure is provided along an annular region on the surface of FIG. 2A for near vision correction, and second multiorder diffractive structure is provided on annular and central regions on the surface of FIG. 2B for distance vision correction.
Figure 2B:
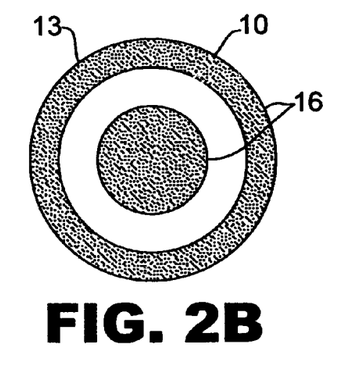

Referring to the FIGS. 1A, 1B and 1C, a bifocal multiorder diffractive (MOD) lens 10 is shown having a lens body 11 with a first surface 12 and a second surface 13 in FIGS. 1A and 1B, respectively. Surfaces 12 and 13 may represent the front and back surface of the lens, respectively. Surface 13 has a first annular region 14 with a MOD lens structure providing a focal distance (or optical power) for near vision correction, and a second region 16 outside the first region 14 with a MOD lens structure having a focal distance (or optical power) for far vision correction. Region 16 represents a central portion 16a and an annular portion 16b. The MOD lens structures of regions 14 and 16 are such as described in the above incorporated U.S. Pat. No. 5,589,982, where the regions have zones with step heights providing the bifocal vision correction at powers in accordance with the eye of the lens user for the desired focal distance. FIGS. 1A–1C represent one embodiment of a bifocal MOD lens where the regions 14 and 16 are formed on the back surface 13 of the lens to divide or split the aperture of lens 10, and the front surface 12 has no diffractive power. The curvature of the lens body 11 in FIG. 1C is for purposes of illustration, the lens body may be other shapes, such as a disk, depending on the particular ophthalmic application. Alternatively, the regions 14 and 16 may be provided on the front surface 12 of the lens, and no power on the back surface 13. FIGS. 2A and 2B represent the front and back surfaces of another embodiment of lens in accordance of the present invention. In this embodiment, bifocal MOD lens 10 has region 14 on the front surface 12 and region 16 on the back surface 13 of the lens to divide the aperture of the lens, rather than on the same surface, as in FIG. 1B. Alternatively, regions 14 and 16 may be provided on back surface 13 and front surface 12, respectively, in FIGS. 2A and 2B. Further, although one annular region 14 is shown, region 14 may have multiple annular regions, alternating with multiple annular portions of region 16.

Figure 3A:
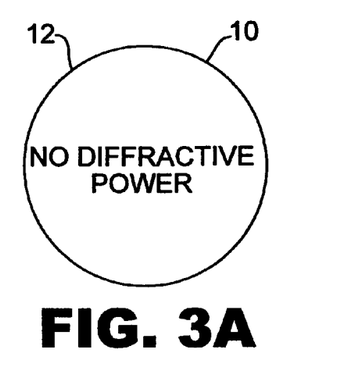
FIGS. 3A and 3B are plan diagrams of the two surfaces of a third embodiment bifocal multiorder diffractive lens of the present invention in which the surface of FIG. 3B has two multiorder diffractive structures along two different regions providing distance and near vision correction, respectively, and the surface of FIG. 3A has no diffractive structures.
Figure 3B:
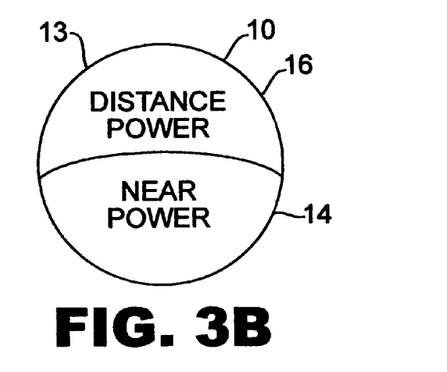
Figure 4A:
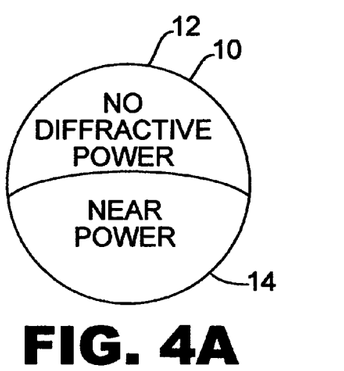
FIGS. 4A and 4B are plan diagrams of the two surfaces of a fourth embodiment bifocal multiorder diffractive lens of the present invention in which each surface has a different diffractive multiorder structure along a region dividing the aperture of the lens for near and distance vision correction.
Figure 4B:
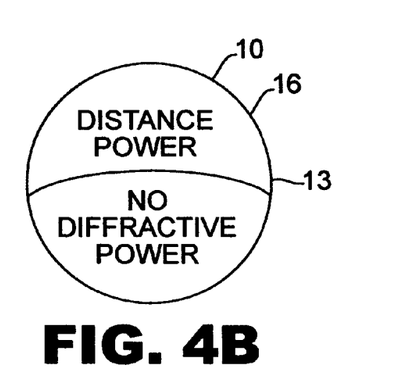

FIGS. 3A and 3B show another embodiment of bifocal MOD lens 10 in which region 16 is formed along a crescent shaped portion substantially occupying the upper part on the lens, and region 14 is formed on the remaining lower portion of the lens to divide the lens aperture. Similarly, regions 14 and 16 in FIGS. 3A and 3B may be on the same surface 12 or 13, or may be split over surfaces 12 or 13 of the lens, as shown in FIGS. 4A and 4B. In FIGS. 3A, 3B, 4A and 4B, surfaces 12 and 13 may represent the front and back surfaces of the lens, or vice versa.

Figure 5:
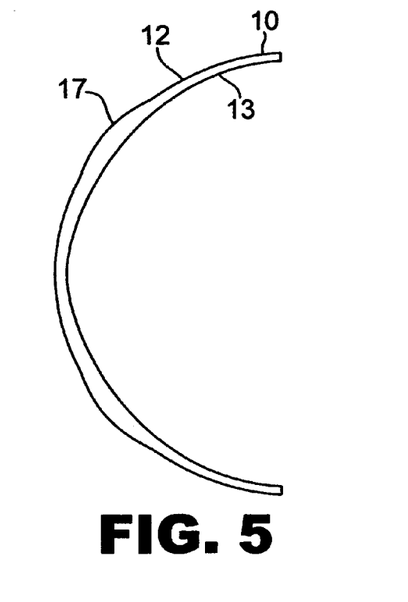
FIG. 5 is a sectional view of a fifth embodiment bifocal multiorder diffractive lens of the present invention having one surface with a multiorder diffractive structure for distance vision correction and refractive curvature along the other surface of the lens for near vision correction.

FIG. 5 shows a further embodiment in a cross-sectional view of bifocal lens 10 having along the entire surface 13 a MOD structure for distance vision correction, and a refractive curvature along annular region 17 along surface 12 to add power for near vision correction without a MOD structure for near vision correction. Although a single annular region 17 is shown, multiple annular regions may be provided along surface 12. Alternatively, the base power of the bifocal lens 10 may be provided by refraction for distance vision correction, and the add power by the MOD structure on surface 13 for near vision correction The lens 10 may be composed of transmissive material, such as typically used in the manufacture of contacts, optic portion of IOLs, or spectacles (e.g., plastic, silicone, glass, or polymers typically used for the particular contact, IOL, or spectacle application). Typical processes providing diffractive optical surface, such as etching or molding, may form the zones of the MOD structures of the lens. For example, single point diamond turning machinery from Precitech, Inc. of Keene, N. H. may be used to provide MOD structures on one or more surfaces of a lens. Although the lens 10 of FIGS. 1A, 1B, 1C, 2A, 2B, 3A, 3B, 4A, 4B, and 5 may be used in a variety of ophthalmic applications, they may be especially useful in the lens of an IOL by incorporation of haptic or support structures used with IOLs, as used in other typical IOL lenses, for example, see U.S. Pat. Nos. 6,406,494, 6,176,878, 5,096,285, or U.S. patent application Publications Nos. 2002/0120329 A1, 2002/0016630 A1, 2002/0193876 A1, 2003/0014107 A1, or 2003/0018385 A1, or without typical haptic structures, as shown in U.S. Pat. No. 4,769,033. Also, regions 14 and 16 shown in the figures may be switched on lenses 10, if desired, depending on the desired portions of the lens aperture divided between near and distance vision correction. FIGS. 1A–1D, 2A, 2B, 3A, 3B, 4A, and 4B show a single optical element providing the body of the lens. The lens 10 may also be provided using multiple optical elements integrated together to provide the body of the lens, as shown below.

Figure 6:
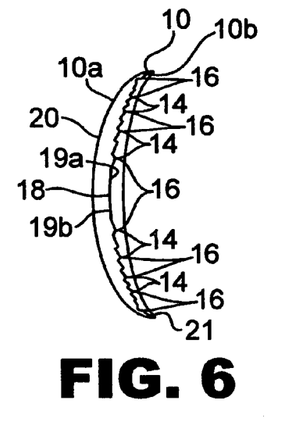
FIGS. 6–8 are sectional views of other embodiments of bifocal multiorder diffractive lenses having two optical elements integrated into a single lens body.
Figure 7:
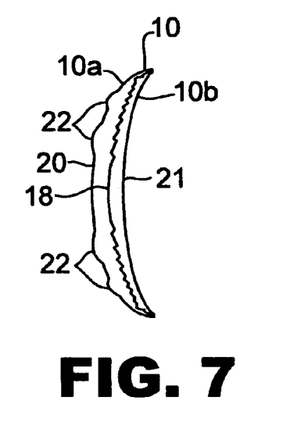
Figure 8:
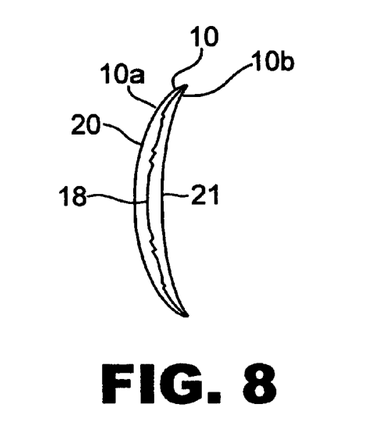

Referring to FIGS. 6–8, embodiments of lens 10 are shown having two optical elements 10a and 10b, in which a diffractive profile is provided on an intermediate surface 18 representing the front surface 19a of optical element 10b, or back surface 19b of optical element 10a, between front surface 20 and back surface 21 of the lens. The surfaces 19a and 19b are shaped (i.e., one surface a diffractive profile and the other surface the reverse diffractive profile) such that they mate with each other when optical elements are bonded (e.g. liquid adhesive), fused, or otherwise sealed together. Optical elements 10a and 10b are made of different materials with different indices of refraction, such that light may properly be diffracted by the MOD structures of regions 14 and 16. The advantage of providing the diffractive structures on an intermediate surface 18 of the lens is that the front and/or back surface of the lens may be substantially smooth, and thus more comfortable when such lens is used as a contact lens. FIG. 6 has a diffractive profile along surface 18 similar to FIG. 1B with a central region 16 and alternating annular regions 14 and 16 at increasing diameters to the edge of lens 10, and the MOD structure of regions 14 provide near vision correction and the MOD structure of regions 16 provide distance vision correction. In the lens 10 of FIG. 6, refractive power of the lens may be zero or minimal. FIG. 7 has annular refractive regions 22 along surface 20 having curvature providing additional power to the lens for near vision correction, and the entire surface 18 may provide a diffractive profile for distance vision correction without a MOD structure for near vision correction. In other words, in FIG. 7 light passing through the refractive regions 22 provides power added to the base power of the MOD structure on surface 18 to enable near vision correction. Although two refractive regions 22 are shown, one or more than two annular regions 22 may be provided. FIG. 8 differs from FIG. 7 in that the base power for distance vision correction is provided by the refractive curvature of the lens 10 body provided by optical elements 10a and 10b, and along surface 18 are annular regions 14 with a MOD structure to add power for near vision correction without a MOD structure for distance correction.

Figure 9:
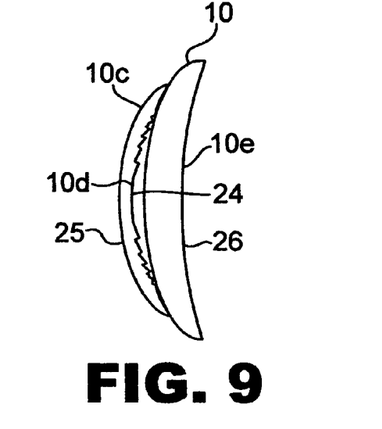
FIGS. 9–14 are sectional views of further embodiments of bifocal multiorder diffractive lenses having three optical elements integrated into a single lens body in which the middle optical element may be air, liquid, or of a solid lens material.
Figure 10:
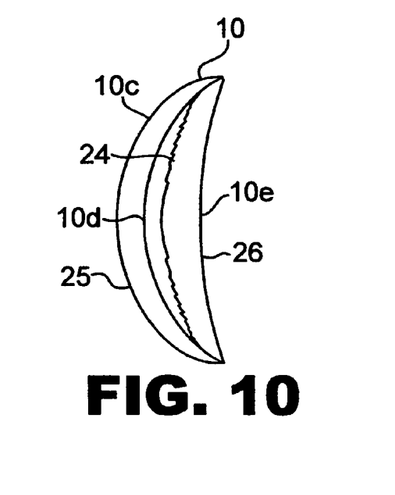
Figure 11:
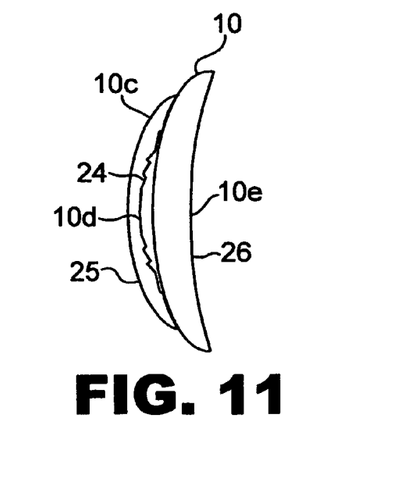
Figure 12:
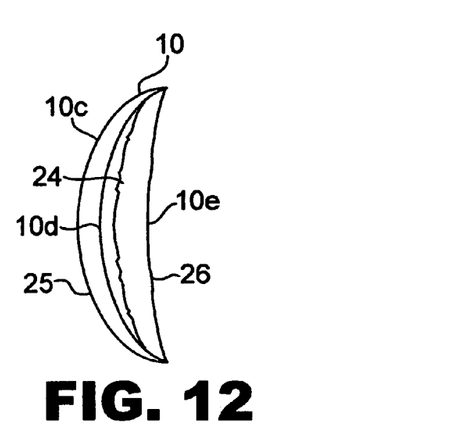
Figure 13:
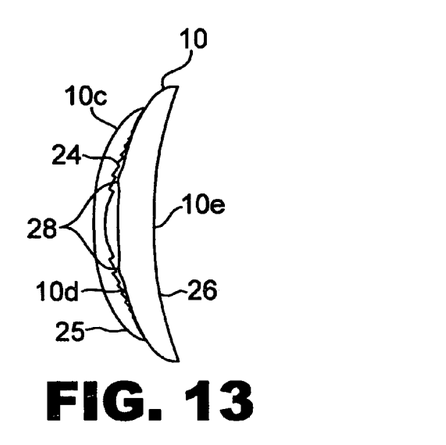
Figure 14:
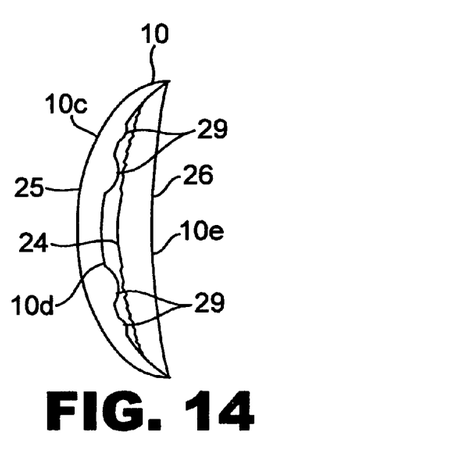

Referring to FIGS. 9–14, embodiments of lens 10 are shown having three optical elements 10c, 10d, and 10e in which a diffractive profile is provided on an intermediate surface 24 between front surface 25 and back surface 26 of the lens. Optical element 10e represents a base, optical element 10c represents a cover, which is bonded (such as by liquid adhesive), fused, or otherwise sealed to the base, and optical element 10d represents air, liquid, or solid lens material occupying the interface between optical elements 10e and 10c. FIG. 9 shows the intermediate surface 24 on the back surface of optical element 10c having MOD structures of regions 14 and 16 segmenting the lens aperture, and is similar to FIG. 1B but with a central region 16 and alternating annular regions 14 and 16 of increasing diameter to the edge of lens 10. Alternatively, intermediate surface 24 may represent the front surface of optical element 10e facing optical element 10d, as shown in FIG. 10. Further, multiple intermediate surfaces 24 between adjacent elements 10c, 10d, and 10e may be provided and the central and annular regions 16 provided on one of such intermediate surfaces, and annular regions 14 on another of such intermediate surfaces to divide the aperture of the lens of FIG. 9 or 10. In the lens 10 of FIGS. 9 and 10 refractive power of the lens may be zero or minimal, but additional refractive power for near or distance vision may be added to the lens body. FIG. 11 shows a lens having surface 24 on the back surface of optical element 10c, and optical elements 10c and/or 10e are shaped to provide refractive curvatures providing a base power to the lens for distance vision correction. In FIG. 11, the diffractive profile of surface 24 has annular regions 14 providing a MOD structure to add power for near vision correction without a MOD structure for distance vision correction. FIG. 12 shows a lens 10 having surface 24 on the front surface of optical element 10e, and having refractive curvatures of lens 10 of optical element 10c and 10e (and element 10d if of a solid optically transmissive material) to provide the base power for distance vision correction, and annular regions on surface 24 with a MOD structure for near vision correction. FIG. 13 shows a lens 10 with intermediate surface 24 on optical element 10d and regions or rings 28 upon the front surface of optical element 10e with curvature adding refractive power for near vision correction. FIG. 14 shows a lens 10 having surface 24 on front of optical element 10e and having regions or rings 29 upon the back surface of optical element 10d with curvature adding refractive power for near vision correction. In FIGS. 13 and 14, a MOD structure is provided on surface 24 for distance visions correction without a MOD structure for near vision correction.

In FIG. 9–14, when optical element 10d is of a solid optically transmission material, rather than air or liquid, it has a shape having reverse surface features to mate with diffractive profile of surface 24 on either elements 10c or 10d, of if present, reverse surface features to mate with refractive features 28 or 29 along elements 10e or 10c, respectively. Further, when optical element 10d is of a solid material it may be bonded, fused, or otherwise sealed to optical elements 10c and/or 10e. Although lenses 10 of FIGS. 6–14 may be used in various ophthalmologic applications, they are especially useful for contact lenses.

Figure 15:
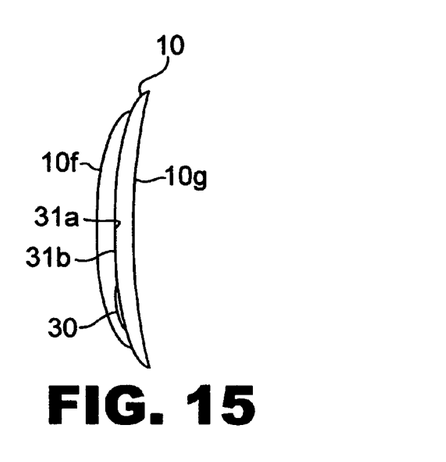
FIG. 15 is a sectional view of an additional embodiment of a bifocal multiorder diffractive lens having two optical elements integrated into a lens body for use as a spectacle lens having a multiorder diffractive structure for near vision correction, and refractive power of the lens body for distance vision correction.

Referring to FIG. 15, another embodiment of the bifocal multiorder diffractive lens 10 is shown having two optical elements 10f and 10g integrated into a single lens body for use as a spectacle lens and a region 30 having a MOD structure for near vision correction, where curvatures along elements 10f and 10g provide refractive power for distance vision correction. Region 30 is formed near the lower part of the lens 10 on either surface 31a of optical element 10f, or surface 31b of optical element 10g. The optical element 10f or 10g not having such region 30f is shaped having a reverse surface features from region 30 to mate with such region when optical elements 10f and 10g are joined together. Except for region 30, the back surface 31a of optical element 10f and front surface 31b of optical element 10g have the same curvature such that they mate with each other when the optical elements are bonded, fused, or otherwise sealed together.

Figure 16:
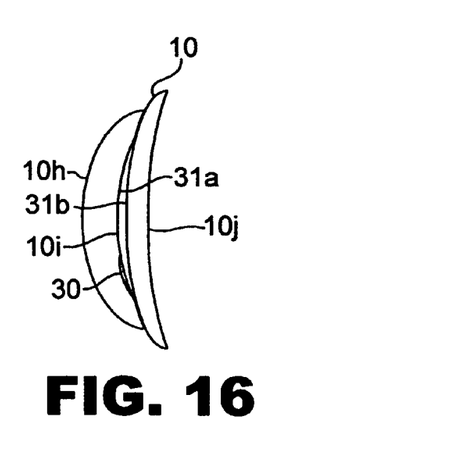
FIGS. 16 and 17 are a sectional views of a still further embodiment of a bifocal multiorder diffractive lens having three optical elements integrated into a lens body for use as a spectacle lens having a multiorder diffractive structure between first and second elements in FIG. 16, and between the second and third elements in FIG. 17, and refractive power of the lens body for distance vision correction.
Figure 17:
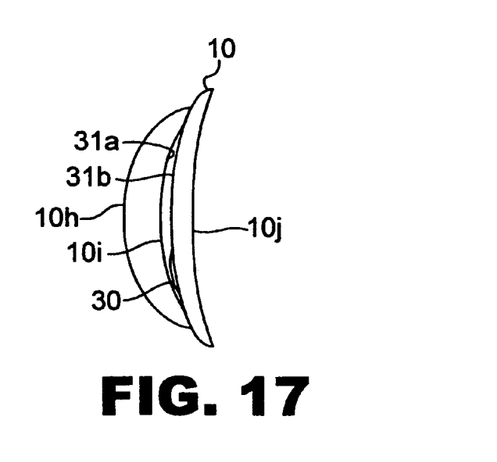

Referring to FIGS. 16 and 17, embodiments of the bifocal multiorder diffractive lens are shown having three optical elements 10h, 10i, and 10j integrated into a single lens body for use as a spectacle lens. Optical element 10j represents a base, optical element 10h represents a cover, which is bonded, fused, or otherwise sealed to the base, and optical element 10i represents air, liquid, or solid lens material occupying the interface between optical elements 10h and 10j. Region 30 having MOD structure for near vision correction may be provided along surface 31a of optical element 10h or surface 31b of optical element 10j, while curvature of optical elements 10h and 10j provide refractive power for distance vision correction. Optionally, a diffractive plate or member may provide region 30, which may be inserted in a space provided between optical elements 10h or 10j prior to joining such elements, and bonded in such space by liquid adhesive or other joining means.

Lenses 10 of FIGS. 6–14 may be made of optically transmissive materials, such as plastic, silicone, glass, or polymer typically used to provide lenses in ophthalmic applications. FIGS. 9, 11, and 13 show the cover optical element 10c as having edges short of the upper and lower edges of the lens 10 for purposes of illustration, optical element 10c, like in FIGS. 10 and 12, may extend to such upper and lower edges of the lens. When lens 10 of FIGS. 6–14 represents a contact lens, surfaces 21 or 26 will contact and conform to the eye surface of the contact lens wearer, as typical of contact lens.

One advantage over bifocal refractive optics of comparable powers is that the lens 10 having bifocal MOD structure is thinner, and more readily foldable when part of the optic portion of an IOL during implantation.

The MOD structures in the embodiments of lens 10 shown in the above described figures may be designed for manufacture in accordance with the equations shown in the above-incorporated U.S. patent. In such equations, n represents the index of refraction between the material (within which the phase profile of the MOD structure is made) and air. However, in the present application, MOD structures may interface with materials other than air, such as liquid (e.g., in the lens, or within which the lens may be immersed as may be the case of an IOL in the eye for the lens having MOD structure on an outer lens surface), or material of adjacent lens elements. Thus, the same equations may be used with "n−1" representing the difference in the index of refraction between the material that the MOD structure will be made and such other material in the particular optical design of lens 10.

The MOD structures in the embodiments of lens 10 shown in the above described figures may be fashioned such that the efficiency of the structure is optimized for human eyes perception of light wavelengths under high illumination, referred to as photopic vision, or lower illumination, referred to as scotopic vision, as generally occurs during day and night natural illumination, respectively. This is achieved by selecting the MOD number p of the MOD lens structure. The optical design of the MOD structure and the variable p is discussed in the above-incorporated U.S. patent. Photopic efficiency describes the spectral response under bright light conditions. The peak photopic efficiency is at $\lambda=555$ nm. Scotopic efficiency describes the spectral response under low light conditions. The peak scotopic efficiency is at $\lambda=507$ nm.

The MOD structures of the lens 10 are designed such that the wavelengths brought to a common focus with high efficiency correspond to these wavelengths. Start by choosing the design wavelength $\lambda_0$ to be one (either photopic or scotopic) of these peaks, for example, $\lambda_0=555$ nm for photopic. The other wavelengths with the same focal length are given by $$\lambda_{peak} = \frac{p\lambda_0}{m}$$

(See Eq. (8) in the above incorporated U.S. patent.) So to bring a wavelength $\lambda_{peak}$ to the same focus as wavelength $\lambda_0$, p and m are found such that $$\frac{\lambda_{peak}}{\lambda_0} = \frac{p}{m}$$

where m is the order number, and p is an integer representing the maximum phase modulation as a multiple of $2\pi$.

For photopic and scotopic peaks, p/m is needed to be 507/555 or 0.914. Since p and m are integers, this equation may not be satisfied exactly for small values of p and m, but approximate solutions for these values may be found. For example, these values may be p=11, m=12; p/m=0.917
p=21, m=23; p/m=0.913
p=32, m=35; p/m=0.914

Figure 18:
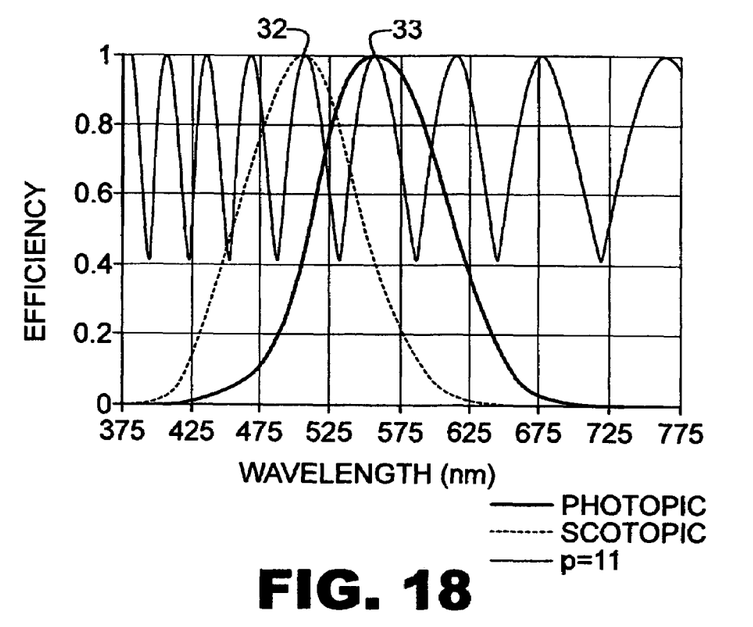
FIGS. 18, 19, and 20 are graphs of the efficiency versus wavelength for three multiorder diffractive structures having different values of p, an integer representing the maximum phase modulation as a multiple of $2\pi$, where the peaks of the efficiency correspond with the peak of human perception of light for photopic and scotopic vision.
Figure 19:
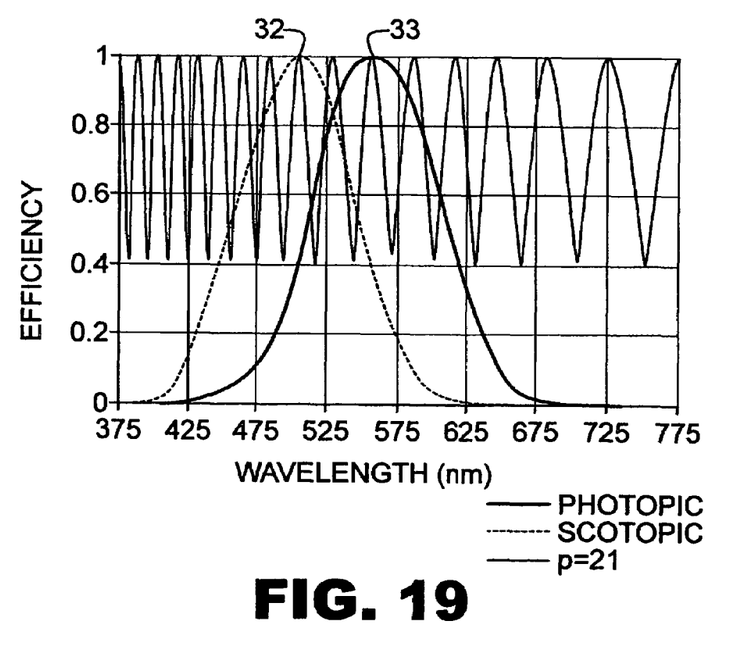
Figure 20:
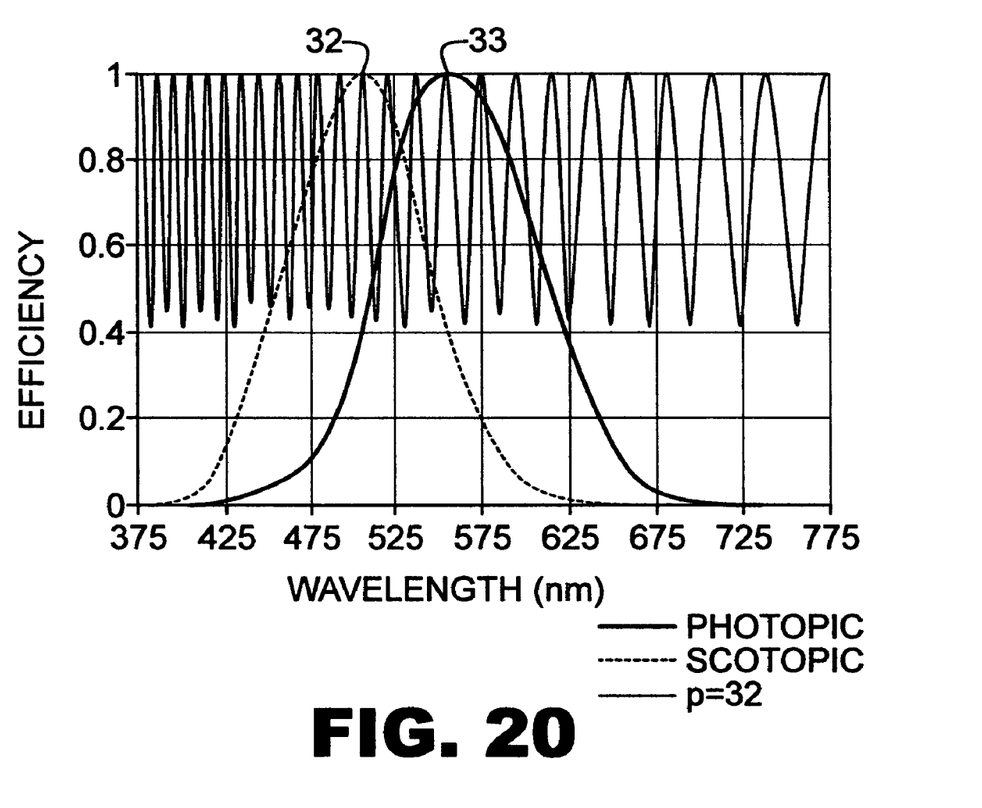

The efficiency curves for these three cases are graphed in FIGS. 18, 19, and 20, respectively, along with the efficiency curves of the human's eye perception of wavelength in bright light, the photopic response, and dim light, the scotopic response. For each MOD structure, a peak aligns with peak scotopic efficiency and another peak aligns with photopic efficiency, as indicated by numerals 32 and 33, respectively. Thus, the amount of light diffracted is maximized at such wavelength for low and high illumination. In the absence of such optimization of the MOD structures on lens 10, the user of the lens may not view light corresponding to the peak scotopic and photopic efficiency of the eye, and thus the perceived intensity of the light from such a lens would appear less to the user than if the MOD structures were so optimized. Although such optimization for photopic and scotopic vision are described for MOD structures in the above bifocal lens 10, the optimization may be provided in a lens having a single MOD structure or any number of MOD structures.

In the MOD structures described for embodiments of lens 10 in the above described figures, astigmatism may also be corrected by use of non-circular zones (hyperbolic or elliptical) in a MOD structure described in the incorporated U.S. patent, such as described in U.S. Pat. No. No. 5,016,977 in non-MOD diffractive structures.

EXAMPLE 1

Consider an ophthalmic lens prescription requiring a correction of −7 diopters for distance vision, with a +2 diopter add power for near vision. Thus, the two powers (denoted by ϕ) of the lens are $\phi_{distance} = -7D$ $\phi_{near} = -5D \ (=-7+2)$ The radial locations ($r_j$) of the diffractive zones from the center of the lens are given by $$r_j = \sqrt{\frac{2jp\lambda_0}{|\phi_0|}}$$

where j is the zone number, p is the MOD number, $\lambda_0$ is the design wavelength, and $\phi_0$ is the desired optical power of the lens. [See Eq. (1) of the above-incorporated U.S. patent, with $\phi_0 = 1/F_0$.]

In this example, $\lambda_0 = 555$ nm (peak of photopic response). If p=11, the zone radii within a clear aperture diameter of 12 mm for the distance power are

Distance power (−7 D)

| ZONE NUMBER (j) | ZONE RADIUS ($r_j$) |
|---|---|
| 1 | 1.320714 |
| 2 | 1.867772 |
| 3 | 2.287544 |
| 4 | 2.641428 |
| 5 | 2.953206 |
| 6 | 3.235076 |
| 7 | 3.494281 |
| 8 | 3.735544 |
| 9 | 3.962142 |
| 10 | 4.176465 |
| 11 | 4.380313 |
| 12 | 4.575088 |
| 13 | 4.761902 |
| 14 | 4.941660 |
| 15 | 5.115104 |
| 16 | 5.282856 |
| 17 | 5.445444 |
| 18 | 5.603315 |
| 19 | 5.756859 |
| 20 | 5.906413 |

Similarly, for the near power, the zone radii are

Near power (−5 D)

| ZONE NUMBER (j) | ZONE RADIUS ($r_j$) |
|---|---|
| 1 | 1.562690 |
| 2 | 2.209977 |
| 3 | 2.706658 |
| 4 | 3.125380 |
| 5 | 3.494281 |
| 6 | 3.827793 |
| 7 | 4.134489 |
| 8 | 4.419955 |
| 9 | 4.688070 |
| 10 | 4.941660 |
| 11 | 5.182856 |
| 12 | 5.413317 |
| 13 | 5.634359 |
| 14 | 5.847051 |

In this example, two different MOD structures are shown for two different prescriptions to correct distance and near vision. The below example shows that such prescriptions may be combined in a lens to provide a multiorder diffractive bifocal lens.

EXAMPLE 2

To construct the bifocal MOD lens along the same surface, as shown in FIGS. 1A–1C, all the diffractive power is contained in circular/annular regions of one surface of the lens. The distance power is contained in regions 16a and 16b of FIG. 1B, while the near power is contained in region 14. We choose the radius of region 16a to be 2 mm, the outer radius of region 14 to be 4 mm and the outer radius of region 16b to be 6 mm. Then, the zone locations for the bifocal lens are the radii of the individual power components that lie within these region boundaries. There are no diffractive zones on the other side of the lens.

Zone locations for bifocal MOD lens

| ZONE NUMBER (j) | ZONE RADIUS ($r_j$) | |
|---|---|---|
| 1 | 1.320714 | distance |
| 2 | 1.867772 | distance |
| 3 | 2.209977 | near |
| 4 | 2.706658 | near |
| 5 | 3.125380 | near |
| 6 | 3.494281 | near |
| 7 | 3.827793 | near |
| 8 | 4.176465 | distance |
| 9 | 4.380313 | distance |
| 10 | 4.575088 | distance |
| 11 | 4.761902 | distance |
| 12 | 4.941660 | distance |
| 13 | 5.115104 | distance |
| 14 | 5.282856 | distance |
| 15 | 5.445444 | distance |
| 16 | 5.603315 | distance |
| 17 | 5.756859 | distance |
| 18 | 5.906413 | distance |

Note that this is one way to combine the zones from the two individual power; other combinations are possible.

EXAMPLE 3

Another option is to place the near power on one surface of the lens and the distance power on the other surface, as in the lens of FIGS. 2A and 2B. In this embodiment, the zone locations are

| ZONE NUMBER (j) | ZONE RADIUS ($r_j$) | |
|---|---|---|
| First Surface | | |
| 1 | 2.209977 | near |
| 2 | 2.706658 | near |
| 3 | 3.125380 | near |
| 4 | 3.494281 | near |
| 5 | 3.827793 | near |

No diffractive zones for radius less than 2.0 mm or radius greater than 4.0 mm.

| | Second Surface | |
|---|---|---|
| 1 | 1.320714 | distance |
| 2 | 1.867772 | distance |
| 3 | 4.176465 | distance |
| 4 | 4.380313 | distance |
| 5 | 4.575088 | distance |
| 6 | 4.761902 | distance |
| 7 | 4.941660 | distance |
| 8 | 5.115104 | distance |
| 9 | 5.282856 | distance |
| 10 | 5.445444 | distance |
| 11 | 5.603315 | distance |
| 12 | 5.756859 | distance |
| 13 | 5.906413 | distance |

No diffractive zones for radius greater than 2.0 mm and less than 4.0 mm.

For all of the above examples, the height of the zones is given by $$h = \frac{p\lambda_0}{n_{lens}(\lambda_0) - n_{medium}(\lambda_0)}$$

[See Eq. (4) of above-incorporated U.S. patent.]

If the lens is in air, then $n_{medium}(\lambda_0)=1.0$. Also, if the lens is constructed of a material with a refractive index of $n_{lens}(\lambda_0)=1.5$, this results in a height of h=12.21 µm, since in these examples p=11 and $\lambda_0$=555 nm. As these examples show, different MOD structures may be produced for lens 10 having the particular desired optical power that may lie on the same or different lens surfaces of the front or back surface of the lens, or on an interior surface in the case of a multi-element lens. Although in Examples 2 and 3 a single annular region provides near vision correction, multiple annular regions for near vision correction may also be provided, which in the case of Example 2 divide the lens aperture with annular regions of the MOD structure for distance vision correction.

In summary, lens 10 may have a segmented aperture providing the bifocal vision correction. Each point in the aperture of the lens only produces a single lens power. The bifocal behavior is provided by having different areas of the lens aperture of different optical powers. This segmentation may be done on one side or on two sides of the lens substrate, as described earlier. When segmentation is done on two sides, the corresponding area on the non-diffractive side has no diffractive power (FIGS. 2A, 2B, 4A, 4B). The power split (i.e., the fraction of the aperture providing distance vision correction and the fraction providing near vision correction) is determined by the fraction of the aperture that is covered by each diffractive lens. Although this ratio will be fixed at manufacture, in use it will be affected by the size of the eye pupil. The aperture may be divided by concentric annular zones, or other divisions of the aperture may be provided, such as shown in FIGS. 3A, 3B, 4A, and 4B. Also, even in a bifocal with only two distinct powers, each power may be provided in more than one optical zone of the lens, in order to maintain the desired power balance over a range of pupil sizes.

In other bifocal lenses described above, a base power may be provided over the entire lens by either refractive (non-diffractive) optional structures, or MOD structures, and add power in a segmented lens portion of a refractive or MOD structure, as in FIGS. 5, 7, 8, and 11–14. The lens 10 having such a hybrid refractive and MOD structures are often useful for bifocal prescriptions where only a relatively small amount of add power (~1 to 2.5 diopters) is required for near vision correction. This additional power can be provided by a weak lens, i.e., a surface with a large radius of curvature or, equivalently, small curvature, while distance vision correction is provided by a MOD structure of the appropriate power. A portion of the lens aperture has a weak refractive surface that provides the add power. The refractive zone (or zones) is located on the opposite side of the lens from the diffractive surface. As a result of the small curvature, the effect on the thickness would be relatively small. An example cross-section of the lens utilizing an annular refractive zone is shown in FIG. 5. As also described above, a hybrid refractive and MOD diffraction lens may have the add power provided by a diffractive component added to a base refractive lens. However, this may increase the thickness of the lens.

Although the lenses described herein are for bifocal lenses to provide two optical powers, it may be extended to trifocal or further number of optical powers by providing additional alternating annular regions with such powers, or refractive regions of different add powers to a diffractive MOD structure base power. Further, each MOD structure is designed for a particular optical power at a design wavelength, in vision applications involving illumination of multiple wavelengths, the power represents a nominal optical power over the range of different wavelengths diffracted by the MOD structure to a common focus, thus at different wavelengths the optical power lies within a range near the optical power at the design wavelength.

From the foregoing description, it will be apparent that there has been provided a bifocal multiorder diffractive lenses for vision correction using MOD structures. Variations and modifications in the herein described device in accordance with the invention will undoubtedly suggest themselves to those skilled in the art. Accordingly, the foregoing description should be taken as illustrative and not in a limiting sense.

What is claimed is:

1. A multiorder diffractive optical element comprising: one or more multiorder diffractive structures in which said one or more diffractive structures are each optimized in accordance with wavelengths for both photopic and scotopic vision.

2. The optical element according to claim 1 wherein said photopic and scotopic vision each have a wavelength of peak efficiency, and the wavelength of peak efficiency for both photopic and scotopic vision aligns with a wavelength of peak efficiency for each of said diffractive structures.

3. The optical element according to claim 1 wherein each of said one or more multiorder diffractive structures directs light in a plurality of different wavelengths to a single focus.

4. The optical element according to claim 1 wherein said optical element is provided by a single body.

5. The optical element according to claim 4 wherein said one or more multiorder diffractive structures are provided on a single surface of said body.

6. The optical element according to claim 4 wherein said one or more multiorder diffractive structures are at least two in number and provided on different surfaces of said body.

7. The optical element according to claim 1 wherein said optical element is provided by multiple optical elements.

8. The optical element according to claim 7 wherein said one or more multiorder diffractive structures are provided on an internal surface of said optical element between two of said multiple optical elements.

9. A multiorder diffractive lens comprising:
at least one multiorder diffractive structure which directs light of a plurality of different wavelengths to a single focus wherein said at least one multiorder diffractive structure is optimized for photopic and scotopic vision.

10. The lens according to claim 9 wherein said photopic and scotopic vision each have a wavelength of peak efficiency, and the wavelength of peak efficiency for both photopic and scotopic vision aligns with a wavelength of peak efficiency for said diffractive structure.

11. The lens according to claim 9 wherein said diffractive structure corrects for astigmatism.

12. The lens according to claim 9 wherein the diffractive structure is characterized by a plurality of zones which define zone boundaries at which light incident on the diffractive structure experiences an optical phase shift, and which diffract light of each of said wavelengths in a different diffractive order, m, such that $m \geq 1$ to the focus for the diffractive structure.

13. The lens according to claim 9 further comprising one or more surfaces providing refractive power to said lens.

14. The lens according to claim 9 wherein said lens is part of an intraocular implant.

15. The lens according to claim 9 wherein said lens represents a contact lens.

16. The lens according to claim 9 wherein said lens represents a spectacle lens.

17. The optical element according to claim 1 wherein each of said one or more multiorder diffractive structures is characterized by a plurality of zones which define zone boundaries at which light incident on the diffractive structure experiences an optical phase shift, and which diffract light of each of said wavelengths in a different diffractive order, m, such that $m \geq 1$ to the focus for the diffractive structure.

18. The optical element according to claim 1 further comprising a lens body having said one or more multiorder diffractive structures, and one or more surfaces providing refractive power.

19. The optical element according to claim 1 wherein one or more of said diffractive structures corrects for astigmatism.

20. The optical element according to claim 1 wherein said one or more multiorder diffractive structures are at least two in number and each provide a different optical power.

21. The optical element according to claim 1 wherein said multiorder diffractive structures numbers two, a first of said diffractive structures provides for near vision correction, and a second diffractive structure provides for distance vision correction.

22. The optical element according to claim 21 further comprising a lens body defining a lens aperture, wherein said first and second of said diffractive structures are each in one or more different regions dividing said lens aperture.

23. The optical element according to claim 1 wherein said optical element is part of an intraocular implant.

24. The optical element according to claim 1 wherein said optical element represents a contact lens.

25. The optical element according to claim 1 wherein said optical element represents a spectacle lens.

26. A multiorder diffractive lens comprising:
two or more multiorder diffractive structures of different optical power, in which at least one of said diffractive structures directs light of a plurality of different wavelengths to a single focus wherein said at least one multiorder diffractive structure is optimized for both photopic and scotopic vision.

27. A multiorder diffractive optical element comprising:
one or more multiorder diffractive structures; and
at least one of said diffractive structures has peak efficiencies at wavelengths corresponding to a plurality of selected wavelengths of peak operation efficiencies, wherein at least two of said plurality of selected wavelengths of peak operation efficiencies are each associated with different amounts of light through said optical element.

28. A multiorder diffractive optical element comprising:
one or more multiorder diffractive structures; and
at least one of said diffractive structures has peak efficiencies at wavelengths corresponding to selected wavelengths of peak operation efficiencies, wherein said selected wavelengths of peak operation efficiencies are two in number and are associated with photopic and scotopic vision, respectively.

29. A multiorder diffractive optical element comprising:
one or more multiorder diffractive structures; and
at least one of said diffractive structures has peak efficiencies at wavelengths corresponding to selected wavelengths of peak operation efficiencies, wherein said diffractive structures number two or more, and at least two of said diffractive structures have different optical powers.

30. The optical element according to claim 29 wherein each of said at least two of said diffractive structures have different optical powers which direct light in different diffractive orders to a different single focus in accordance with their respective optical power, thereby providing an optical element which is multifocal.

* * * * *